United States Patent
O'Dowd et al.

(10) Patent No.: US 7,465,312 B2
(45) Date of Patent: Dec. 16, 2008

(54) SYSTEMS AND METHODS FOR TREATING SUPERFICIAL VENOUS MALFORMATIONS LIKE SPIDER VEINS

(75) Inventors: Killian O'Dowd, Dublin (IE); Anthony Jakubowski, Montgomery, IL (US); Edward George Mackay, II, Largo, FL (US); Aidan Mulloy, Dublin (IE); Alan A. Creamer, Carlsbad, CA (US); Sherif Sultan, Galway (IE)

(73) Assignee: Green Medical, Inc., Montgomery, IL (US)

( * ) Notice: Subject to any disclaimer, the term of this patent is extended or adjusted under 35 U.S.C. 154(b) by 330 days.

(21) Appl. No.: 11/446,800

(22) Filed: Jun. 5, 2006

(65) Prior Publication Data

US 2007/0260228 A1    Nov. 8, 2007

Related U.S. Application Data

(60) Provisional application No. 60/796,656, filed on May 2, 2006.

(51) Int. Cl.
*A61N 5/06* (2006.01)

(52) U.S. Cl. .............................. 607/88; 607/89; 606/7; 606/9; 128/898

(58) Field of Classification Search ............. 607/88–92; 606/3–12; 128/898
See application file for complete search history.

(56) References Cited

U.S. PATENT DOCUMENTS

| | | | |
|---|---|---|---|
| 4,111,564 A | 9/1978 | Trice, Jr. | |
| 5,171,749 A | 12/1992 | Levy et al. | |
| 5,258,453 A | 11/1993 | Kopecek et al. | |
| 5,283,255 A | 2/1994 | Levy et al. | |
| 5,298,502 A | 3/1994 | Halling et al. | |
| 5,399,583 A | 3/1995 | Levy et al. | |
| 5,407,808 A | 4/1995 | Halling et al. | |
| 5,514,669 A | 5/1996 | Selman | |
| 5,634,922 A | 6/1997 | Hirano et al. | |
| 5,913,884 A | 6/1999 | Trauner et al. | |
| 6,059,820 A | 5/2000 | Baronov | |
| 6,083,217 A | 7/2000 | Tankovich | |
| 6,102,696 A | 8/2000 | Osterwalder et al. | |
| 6,275,726 B1 | 8/2001 | Chan et al. | |
| 6,319,273 B1 * | 11/2001 | Chen et al. ............ | 607/88 |
| 6,663,659 B2 * | 12/2003 | McDaniel ............. | 607/88 |
| 6,764,501 B2 | 7/2004 | Ganz | |
| 6,783,541 B2 | 8/2004 | Stephens et al. | |
| 6,827,926 B2 | 12/2004 | Robinson et al. | |
| 6,887,862 B2 | 5/2005 | Rychnovsky | |
| 6,936,043 B2 * | 8/2005 | Peyman ................. | 606/4 |

(Continued)

FOREIGN PATENT DOCUMENTS

WO    WO 90/11797    10/1990

(Continued)

*Primary Examiner*—Ahmed M Farah
(74) *Attorney, Agent, or Firm*—Ryan Kromholz & Manion S.C.

(57) ABSTRACT

Systems and methods treat superficial venous malformations, such as spider veins. The systems and methods distribute a light-reactive agent, e.g., verteporfin, at or near an inner wall of a vein. The systems and methods activate the light-reactive agent by applying non-thermal light energy at a wavelength that activates the light-reactive agent to cause localize injury to the inner wall of the vein.

5 Claims, 8 Drawing Sheets

U.S. PATENT DOCUMENTS

| | | | |
|---|---|---|---|
| 7,364,574 B2 * | 4/2008 | Flower | 606/4 |
| 2001/0022970 A1 | 9/2001 | Dees et al. | |
| 2002/0095197 A1 | 7/2002 | Lardo et al. | |
| 2002/0173780 A1 | 11/2002 | Altshuler et al. | |
| 2002/0183301 A1 | 12/2002 | Rychnovsky | |
| 2002/0193850 A1 | 12/2002 | Selman | |
| 2003/0069219 A1 | 4/2003 | Detty et al. | |
| 2003/0082101 A1 | 5/2003 | Taylor et al. | |
| 2003/0100934 A1 | 5/2003 | Stephens et al. | |
| 2003/0233138 A1 | 12/2003 | Spooner | |
| 2004/0044304 A1 | 3/2004 | Hill et al. | |
| 2004/0054370 A1 | 3/2004 | Given | |
| 2004/0147501 A1 | 7/2004 | Dolmans et al. | |
| 2004/0171601 A1 | 9/2004 | Fukumura et al. | |
| 2004/0176345 A1 | 9/2004 | Lavie | |
| 2005/0137180 A1 | 6/2005 | Robinson et al. | |
| 2005/0143793 A1 | 6/2005 | Korman et al. | |
| 2005/0154049 A1 | 7/2005 | Dees et al. | |
| 2005/0215987 A1 | 9/2005 | Slatkine | |
| 2005/0282889 A1 | 12/2005 | Dees et al. | |
| 2006/0020260 A1 | 1/2006 | Dover et al. | |

FOREIGN PATENT DOCUMENTS

| | | |
|---|---|---|
| WO | WO 98/04318 | 2/1998 |
| WO | WO 01/54579 | 8/2001 |
| WO | WO 01/68162 | 9/2001 |
| WO | WO 01/72277 | 10/2001 |
| WO | WO 02/17185 | 2/2002 |
| WO | WO 02/47794 | 6/2002 |
| WO | WO 03/47682 | 6/2003 |
| WO | WO 2004/024273 | 3/2004 |
| WO | WO 2005/004737 | 1/2005 |

* cited by examiner

Localized Cell Injury and Death

SYSTEMS AND METHODS FOR TREATING SUPERFICIAL VENOUS MALFORMATIONS LIKE SPIDER VEINS

RELATED APPLICATION

This application claims the benefit of U.S. Provisional Patent Application Ser. No. 60/796,656, filed May 2, 2006, and entitled "Systems and Methods for Treating Superficial Venous Malformations Like Spider Veins," which is incorporated herein by reference.

BACKGROUND OF THE INVENTION

As the large group of so-called baby-boomers advances in age, there are increasing demands for effective, non-invasive treatment of vascular diseases or dysfunctions affecting the vascular system. There are also increasing demands for non-invasive cosmetic surgery to repair conditions that have vascular origins.

For example, spider veins result from various dysfunctions in the veins. Veins carry oxygen-poor blood from the body back to the heart.

Spider veins can be caused by the backup of blood, when one-way flap valves in veins become weak, causing blood to collect in veins. Spider veins can also arise due to other causes, e.g., hormone changes, inherited factors, and exposure to the sun. Spider veins are often red or blue and close to the surface of the skin. They can look like tree branches or spider webs with their short jagged lines. Spider veins can be found on the legs and face. They can cover either a very small or very large area of skin.

Sclerotherapy is a common treatment for spider veins. Sclerotherapy involves the injection of a solution into the vein that causes the vein walls to swell, stick together, and seal shut. This stops the flow of blood and the vein turns into scar tissue. Microsclerotherapy uses special solutions and injection techniques that can increase the success rate for removal of smaller spider veins. Sclerotherapy involves tedious, hard to learn injection techniques. It can lead to side effects like stinging or painful cramps where the injection was made, or temporary red raised patches of skin, or skin sores, or bruises. The treated vein can also become inflamed or develop lumps of clotted blood. Applying heat and taking aspirin or antibiotics can relieve inflammation. Lumps of coagulated blood can be drained.

Laser surgery can be used to treat larger spider veins in the legs. Laser surgery sends very strong bursts of light onto the vein, which makes the vein slowly fade and disappear. Laser surgery is more appealing to some patients because it does not use needles or incisions. Still, when the laser hits the skin, the patient can feel a heat sensation that can be quite painful. Laser surgery can cause redness or swelling of the skin, and can cause burns and scars. Depending on the severity of the veins, two to five treatments (15 to 20 minutes each) are generally needed to remove spider veins in the legs. Moreover, for spider veins larger than 3 mm, laser therapy is not very practical. Furthermore, the capital cost for purchasing trans-dermal lasers can be quite high, making the treatment relatively costly.

There is need for devices, systems, methods, and protocols that provide minimally invasive, cost effective, and patient-friendly surgical and/or cosmetic surgical treatment of superficial venous malformations, such as e.g., in the treatment of spider veins. There is also a need for devices, systems, methods, and protocols that provide minimally invasive, cost effective, and patient-friendly treatment of diseases or dysfunctions in any region of the body that can be readily accessed by treatment agents carried by blood; e.g., cancers like breast and prostrate cancer; ear, nose, and throat conditions; periodontal disease; and diseases of the eye.

SUMMARY OF THE INVENTION

The invention provides devices, systems, methods, and protocols that provide minimally invasive, cost effective, and patient-friendly surgical and/or cosmetic surgical treatment of superficial venous malformations, e.g., spider veins.

The invention also provides devices, systems, methods, and protocols that provide minimally invasive, cost effective, and patient-friendly surgical treatment of diseases or dysfunctions in regions of the body that can be readily accessed by treatment agents carried by blood; e.g., cancers like breast and prostrate cancer; ear, nose, and throat conditions; periodontal disease; and diseases of the eye.

According to one aspect of the invention, the devices, systems, and methods distribute a light-reactive agent at, in, or near an inner wall of a vein. The devices, systems, and methods activate the light-reactive agent by applying light energy at a wavelength that activates the light-reactive agent to cause localize injury to the inner wall of the vein. The light energy is desirably non-thermal and is generated by a low voltage photoactivation device, comprising, e.g., one or more light-emitting diodes. In one embodiment, the light-reactive agent comprises verteporfin that is administered intravenously. Devices, systems, and methods that incorporate this aspect of the invention can treat superficial venous disease, like spider veins.

The devices, systems, and methods improve the quality of patient care. The devices, systems, and methods eliminate side effects such as bruising, burning, and skin discoloration. The devices, systems, and methods do not require tedious, hard to learn injection techniques. They do not require high cost trans-dermal lasers. The devices, systems, and method are usable by a large group of practitioners, such as dermatologists, phlebologists, vascular surgeons, and interventional radiologists.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
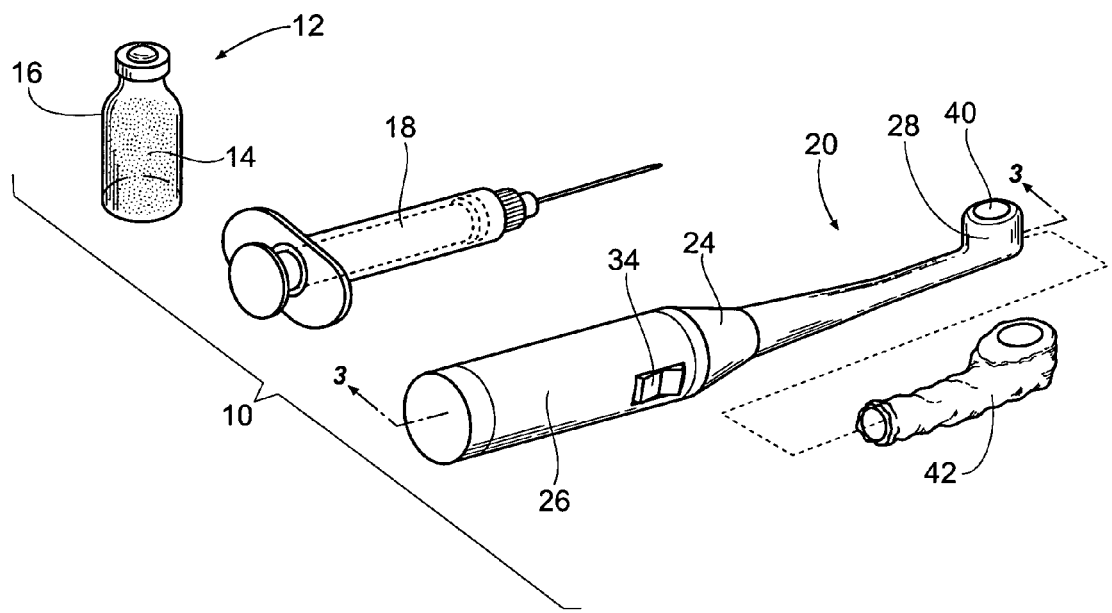
FIG. 1 is a perspective view of a system of devices for treating a superficial venous disease, such as spider veins using a light-reactive agent, the agent being suited for intravenous injection.

FIG. 1 shows devices that together comprise a system 10 for treating a vascular disease or a dysfunction affecting the vascular system using light-reactive agents. The devices and system 10, and their associated methods of use, are particularly well suited for treating superficial venous diseases, such as spider veins. For this reason, the devices and system 10, and their associated methods of use will be described in this context.

Still, it should be appreciated that the disclosed devices and system 10, and their associated methods of use are applicable for use in treating other diseases or dysfunctions elsewhere in the body that are not necessarily related to spider veins or their cause, but are nevertheless capable of treatment by light-reactive agents carried by blood. Other conditions that can be treated by light reactive agents using the system 10 or a form of the system 10 include cancer, e.g., breast or prostrate cancer; conditions of the ear, nose, or throat; periodontal disease; and conditions of the eye or sight (ophthalmology).

As FIG. 1 shows, the system 10 includes at least one source 12 of a selected light reactive agent 14. The source 12 can be provided in various forms. For example, as shown in FIG. 1, the source 12 can comprise a conventional vial 16 containing the light reactive agent 14 in solution suited for intravenous injection. Alternatively, the source 12 can comprise the light reactive agent 14 packaged with a carrier in tablet or capsule form for oral ingestion; or incorporated into a cream that can be applied topically to the skin.

The light reactive agent 14 can comprise any light-reactive drug suited for photodynamic therapy (PDT). PDT is a treatment that uses an agent or drug, also called a photosensitizer or photosensitizing agent, and light energy of a particular selected wavelength. The photosensitizers, which are inert by themselves, bind to proteins found in blood, e.g., lipoproteins. The proteins act as carriers, transporting the photosensitizers to cells targeted for treatment. When exposed to light of the particular wavelength (which varies according to the photosensitizer), the photosensitizer reacts with oxygen. The reaction transforms the oxygen into singlet oxygen and free radicals. The singlet oxygen and free radicals disrupt normal cellular functions and cause cell death.

The light reactive agent 14 can be selected among a group of photosensitizers, depending upon type and location of tissue being treated, as well as the mode contemplated for its introduction into body tissue. Each photosensitizer is activated by light of a specific wavelength. This wavelength determines how far the light can travel into the body. Thus, the physician can select a specific photosensitizer and wavelength(s) of light to treat different areas of the body.

In use, whatever the form, the selected light reactive agent 14 is administered by the system 10 for delivery to a targeted tissue treatment site at, in, or near an inner wall of a vein. In the context of the illustrated embodiment, the targeted tissue site is a sub-dermal region where one or more spider veins are present (this is shown FIG. 4 and will be described in greater detail later).

Figure 15:
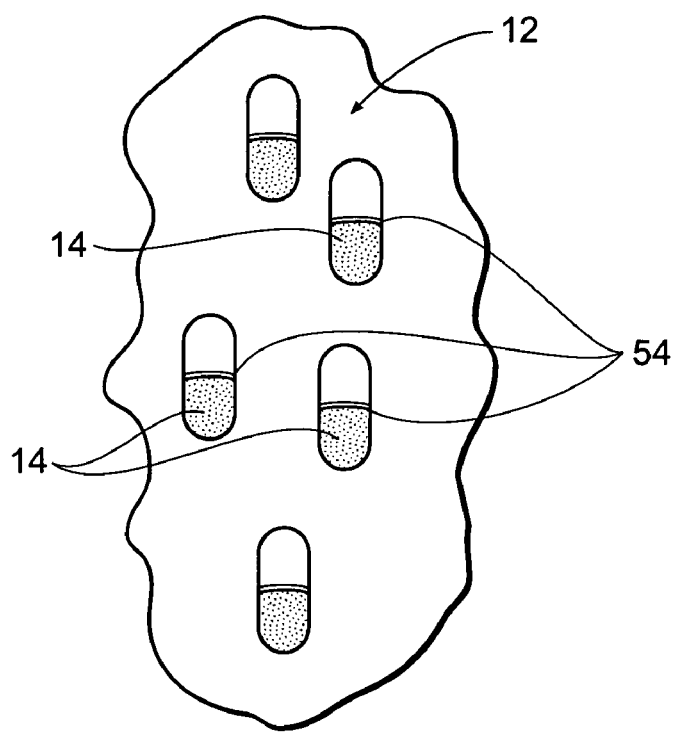
FIG. 15 shows an alternative embodiment of a source of a light-reactive agent usable with the system shown in FIG. 1, the agent being in tablet or capsule form, for oral ingestion.
Figure 16:
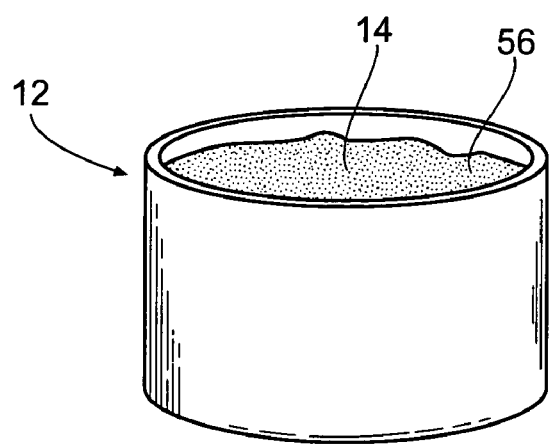
FIG. 16 shows an alternative embodiment of a source of a light-reactive agent usable with the system shown in FIG. 1, the agent being in cream form for topical application.

The form for administration will depend upon the form of the source 12. The light reactive agent 14 can be provided in tablet or capsule form 54 (see FIG. 15), which can be ingested orally for absorption by the GI tract for systemic distribution by blood to the targeted tissue treatment site. The light reactive agent 14 can be incorporated into a cream form 56 (see FIG. 16), and the light reactive agent 14 can be applied topically for percutaneous absorption by the skin to the targeted tissue treatment site.

It has been discovered that an injectable form of the porphyrin-based photosensitizer called verteporfin—commercially available from QLT, Inc. as VISUDYNE® material (verteporfin for injection)—can be intravenously administered to effectively treat spider veins using the system 10 shown in FIG. 1. Therefore, FIG. 1 shows the light reactive agent 14 in solution in the vial 16.

VISUDYNE® material has been used, together with a special laser light, to treat abnormal blood vessel formation in the eye, called age-related macular degeneration (AMD) (which, if untreated, can lead to loss of eyesight). VISUDYNE® material can be activated by shining a pre-calculated dose of light at a particular (wavelength 689 nm) by a low-energy laser or light source 12 into the affected area of tissue.

Figure 6:
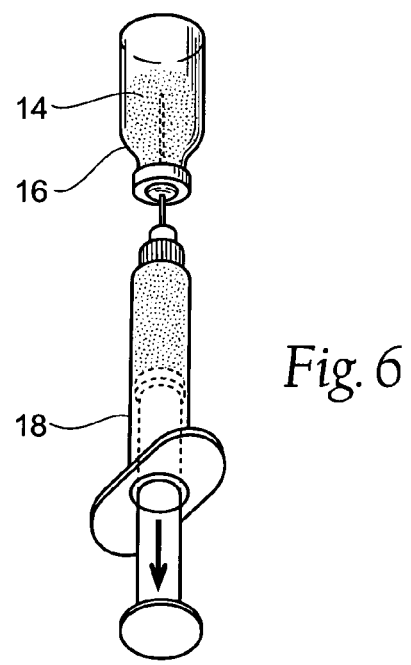
Figure 7:
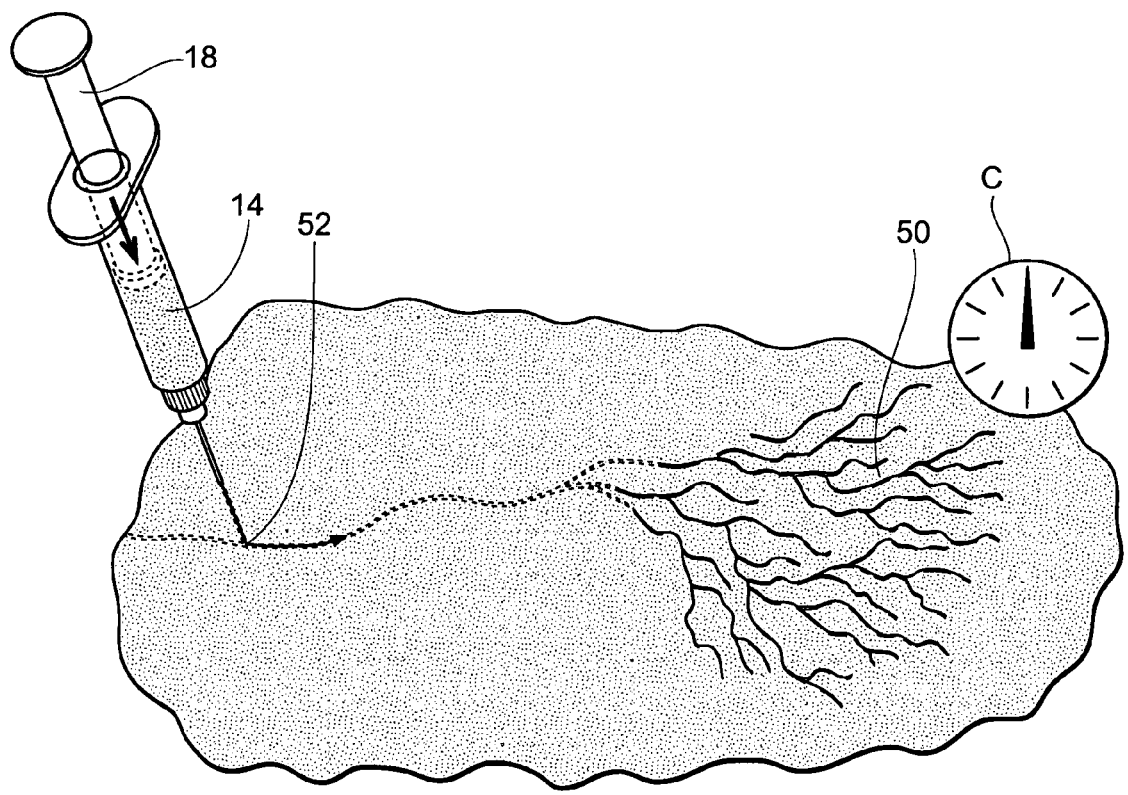
Figure 8:
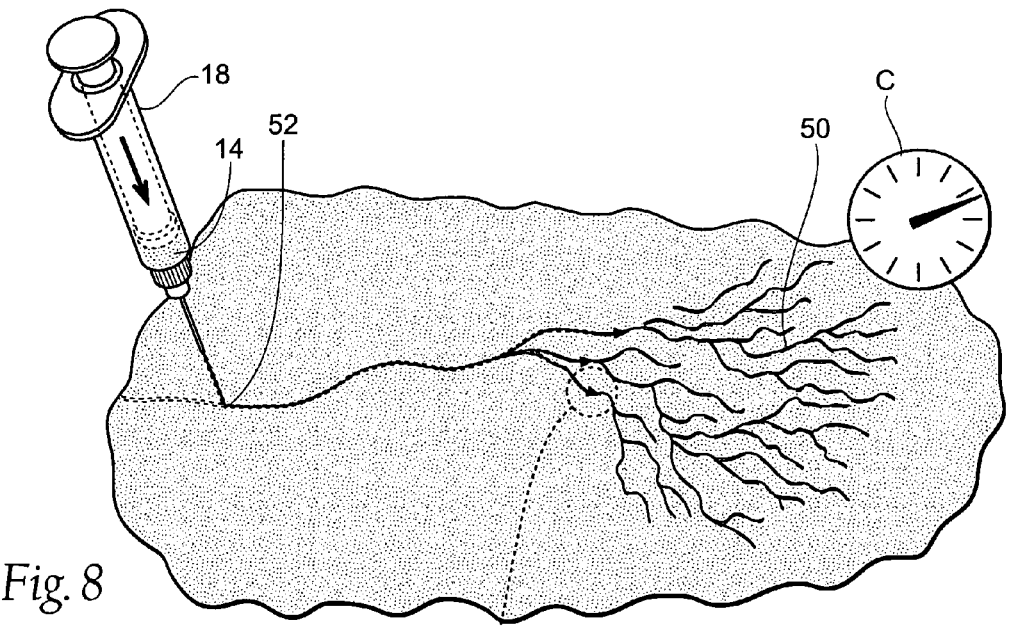

In the context of the illustrated embodiment, where the source 12 comprises an injectable solution of the light reactive agent 14, the device takes the form of a conventional hand-held syringe 18. The syringe 18 draws the light reactive agent 14 in solution from the vial 16 (as shown in FIG. 6) and injects the photodynamic material in solution into the vascular system for transport by the blood flow to the targeted tissue site (as shown in FIG. 7). Instead of a handheld syringe 18, the administration device can take the form of a conventional intravenous (IV) delivery catheter or set coupled to a syringe or other intravenous delivery device or pump.

Figure 3A:
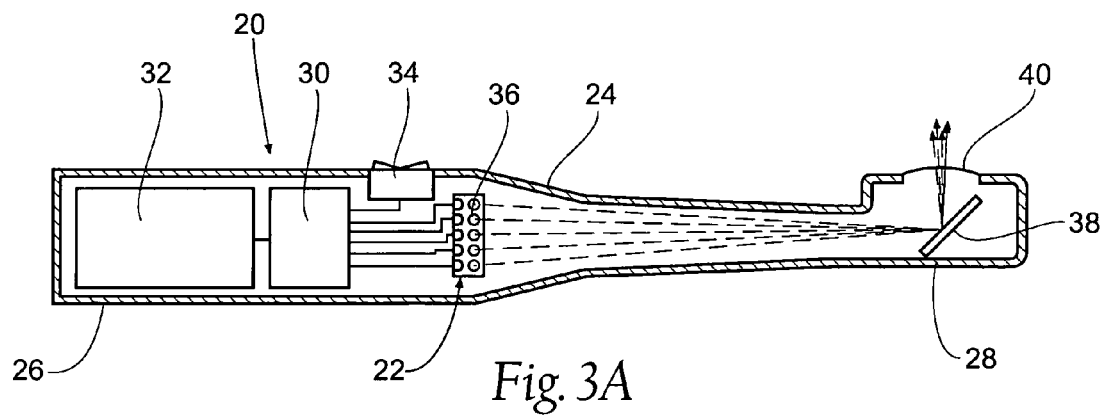
FIGS. 3A and 3B are side section views, taken generally alone line 3-3 in FIG. 1, showing alternative embodiments of the internal components of a photoactivation device that forms a part of the system shown in FIG. 1.

As FIG. 1 also shows, the system 10 includes a photoactivation device 20. The photoactivation device 20 includes one or more light sources 22 (see FIG. 3). The light sources 22 have a wavelength or a range of wavelengths. The photoactivation device 20 also includes means for controlling the intensity or a range of intensities, spot size or a range of spot sizes, and other operating characteristics of the light sources 22 that are conducive to activation the light reactive agent 14 in a desired manner. Desirably, the photoactivation device 20 comprises non-thermal light energy generated by a low-voltage source (not greater than 12 Volts).

The photoactivation device 20 can take various forms, depending upon nature, location, and size of the targeted tissue region. The photoactivation device 20 can, e.g., be mounted on an adjustable frame that is located above or below the targeted tissue region of an individual. The photoactive device may, alternatively, deliver light through fiber optic cables and the like to areas inside the body. For example, a fiber optic cable can be inserted through an endoscope into a targeted internal tissue region (e.g., within a vessel or hollow organ) to treat a dysfunction. Alternatively, the photoactivation device 20 may comprise a portable light source that applies light to surface tissue.

In the context of the illustrated embodiment (see FIGS. 1 and 3A/3B), the photoactivation device 20 is sized and configured to be held and manipulated in a single hand, so that it can be wanded or waved to apply light percutaneously to a tissue region where the spider vein or veins are located.

In this embodiment (see FIGS. 3A and 3B), the photoactivation device 20 includes a low-energy light source 22 carried within a housing 24. The housing 24 comprises a handle end 26 and a light transmitting end 28. The handle end 26 is sized and configured to be conveniently gripped by a practitioner.

The handle end 26 encloses a control circuit 30 coupled to a self-contained low voltage (i.e., no more than 12 volts), DC power source 32, such as a battery. The battery 32 is desirably rechargeable, e.g., by a plug-in connector (not shown), or, alternatively, the battery 32 can be configured to be removed and replaced through a lift-off cover (also not shown). The handle end 26 includes an on-off switch 34, which activates the control circuit 30.

The light source 22 comprises one or more light emitters 36, which are carried within the housing 24 for transmitting light from the light transmitting end 28 of the housing 24. The light emitters 36 are coupled to the control circuit 30.

In use, light can be applied to the skin in a tissue region where the spider vein or veins are located by holding the light transmitting end 28 of the housing 24 out of direct surface contact with the skin. Alternatively, light can be applied to the skin in a tissue region where the spider vein or veins are located by placing the light transmitting end 28 of the housing 24 in direct surface contact with the skin. With direct surface contact between the skin and the light transmitting end 28, reflectance toward the operator is minimized. With direct surface contact between the skin and the light transmitting end 28, the skin acts as a light guide, allowing output flux to be maximized without localized heating.

The light emitters 36 can be, e.g., light emitting diodes (LED's), emitting light in the wave-length(s) that activates the light reactive agent 14. The light emitting diodes of a single photoactivation device 20 can be conditioned to deliver multiple wavelengths, so that the photoactivation device 20 can provide a universal platform for different light reactive agents 14. In the illustrated embodiment, where the light reactive agent 14 is verteporfin, at least one of the wavelengths is 689 nm. In this arrangement, the control circuit 30 may comprise a printed circuit board on which the LED's are mounted.

The light emitters 36 can be arranged in an array sized and configured to focus at common point. Small micro lenses (not shown) may be used to improve focus and adjust the focal distance. In the embodiment illustrated in FIG. 3A, the light emitters 36 are oriented to focus at a reflecting device 38 carried within the light transmitting end 28. The reflecting device 38 reflects the light from the light emitters 36 out a portal 40 on the light transmitting end 28. The reflecting device 38 may comprise, e.g., a surface mirror or a prism. The common focal point for all the light emitters 36 may be slightly short of the reflecting device 38 or slightly beyond the reflecting device 38, so that the light from the reflecting device mirror will spread to cover an area, or spot size, beyond the portal 40. The reflecting device 38 may be made adjustable to change the spot size during use.

Desirably, for ease of handling, the portal 40 is oriented at an angle to the main axis of the housing 24, preferably at about 90°. If desired, the light transmitting end 28 could be mounted for pivoting through a range of angles relative to the main axis, and/or for rotation about the main axis, to permit virtually infinite alignment of the emitted light path with the targeted tissue treatment site.

Figure 3B:
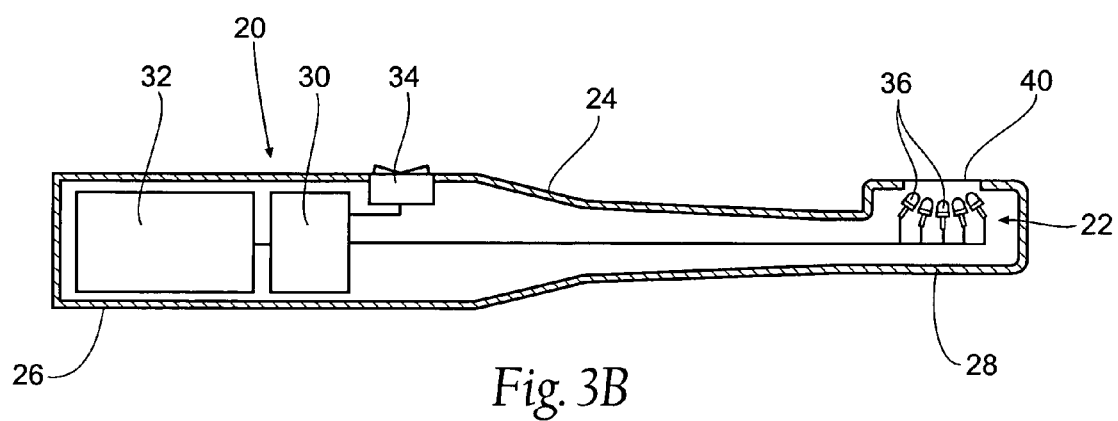

Alternatively, as shown in FIG. 3B, the light-emitters 36 can comprise an array of light emitting diodes carried in the portal 40, for applying diffused light directly from the portal 40 without use of a reflecting device.

As FIG. 1 shows, a removable transparent cover 42 can be provided to cover light transmitting end 28 during use. The cover 42 can comprise, e.g., plastic film encircled with an elastic material. The materials is selected to be substantially transparent to the wavelength of the light emitted. Following use for a given individual, the cover 42 can be removed and discarded, and replaced with a new cover for the next individual.

Figure 2:
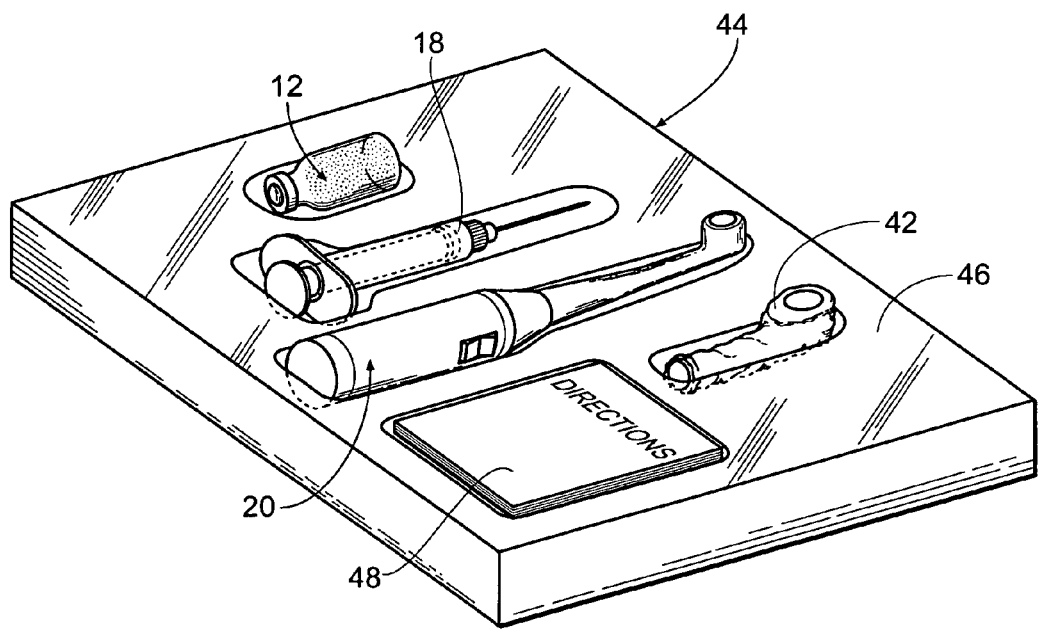
FIG. 2 is a perspective view of the system shown in FIG. 1 packaged as a kit, with directions for using the devices to treat a superficial venous disease.

As FIG. 2 shows, the various components of the system 10 as just described can be consolidated for use in a functional kit 44. The kit 44 can take various forms. In the illustrated embodiment, the kit 44 comprises a sterile, wrapped assembly including an interior tray 46 made, e.g., from die cut cardboard, plastic sheet, or thermo-formed plastic material, which hold the contents. The kit 44 also preferably includes directions 48 for using the contents of the kit 44 to carry out a desired procedure.

In the illustrated embodiment, every component of the system 10 is contained within the kit 44. Of course, various components can be provided in separate packaging. In this arrangement, the directions 48 still instruct use of the various components separately provided as a system 10.

The directions 48 can, of course vary. The directions may be physically present in the kit 44, but can also be supplied separately. The directions 48 can be embodied in separate instruction manuals, or in video or audio tapes, CD's, and DVD's. The instructions for use can also be available through an internet web page. The directions 48 instruct the practitioner how to use the system 10 to carry out the intended therapeutic treatment. The directions 48 incorporate a method of treatment using the system 10.

Figure 4:
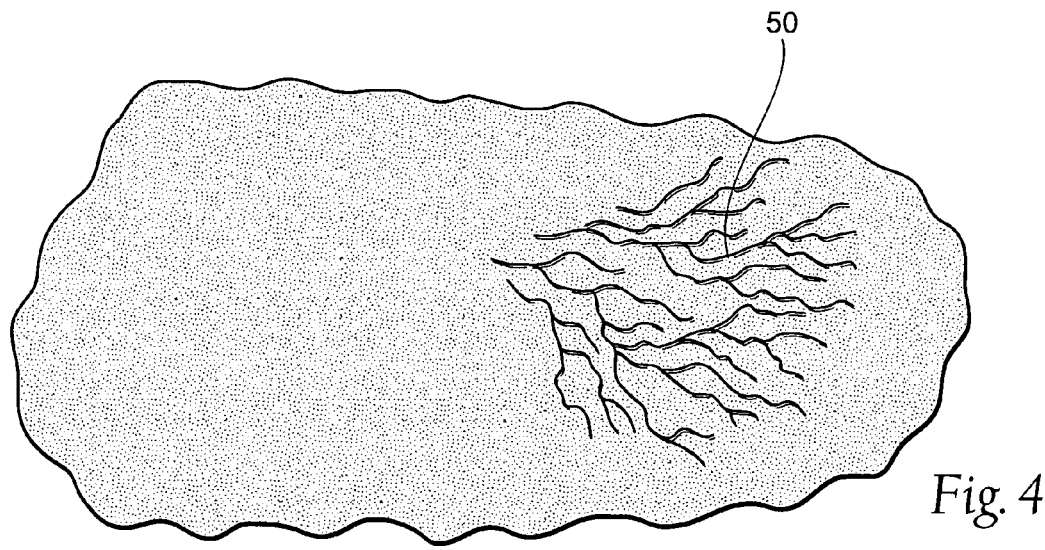
FIGS. 4 to 14 show a representative method of using a system like that shown in FIG. 1 to treat spider veins.

FIGS. 4 to 14 show a representative method of using the system 10 shown in FIG. 1 to treat a vascular condition such as spider veins, which the directions 48 can express in part or in its entirety. As FIG. 4 shows, the method identifies a site where the targeted condition exists, i.e., where the spider veins are present. This site is called the targeted treatment site 50. The spider veins are usually easily identifiable by a trained practitioner. They are often red or blue and close to the surface of the skin. They possess branches or "spider webs" with short jagged lines. Spider veins can be found on the legs and face. They can cover either a very small or very large area of skin.

Figure 5:
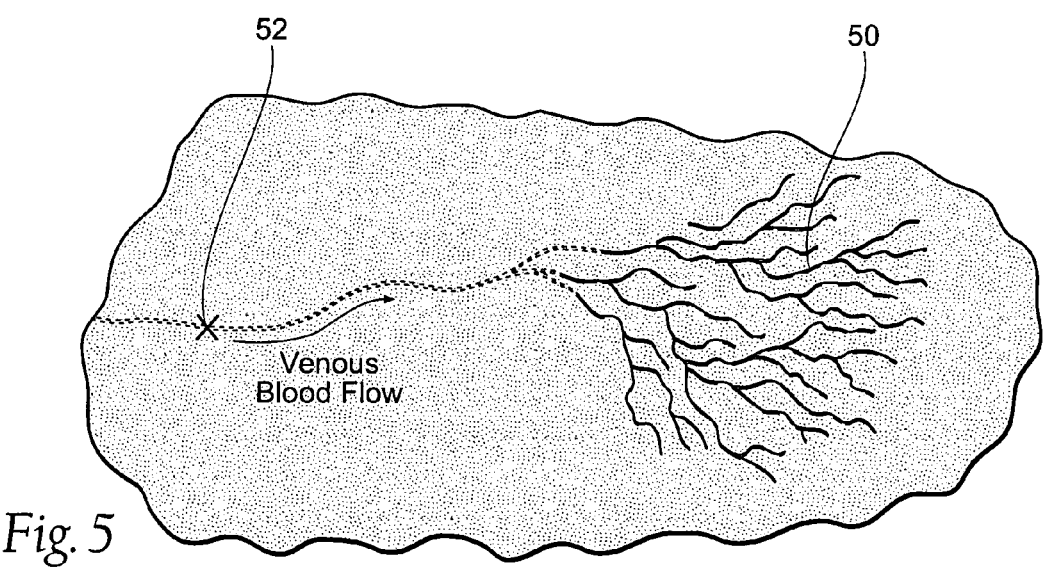

In the illustrated embodiment, the light reactive agent 14 is to be administered intravenously. In this arrangement, an appropriate injection site 52 is identified, as shown in FIG. 5. The injection site 52 is where a selected light reactive agent 14 will administered intravenously by the system 10 for delivery to the targeted treatment site 50. Desirably, the injection site 52 offers venous access at a distance from the targeted treatment site 50 in an upstream blood flow direction (i.e., the injection site 52 is farther from the heart than the treatment site 50). In this manner, the light reactive agent 14, when injected intravenously, is allowed to become systemic and will be conveyed by venous blood flow toward the heart to the targeted treatment site 50.

As FIG. 6 shows, the method prepares the light reactive agent 14 for introduction. In the illustrated embodiment, prescribed volume of the light reactive agent 14 is drawn into the syringe 18. The volume to be injected in dependent upon the therapeutic dose that is prescribed, which is, in turn, dependent upon the concentration of the light reactive agent 14 in solution, as well as the morphology of the targeted treatment site 50.

Typically, VISUDYNE® material is commercially reconstituted in saline or glucose solution at desired concentration of about verteporfin 2 mg/mL. At this concentration, a typical dose for a spider vein region can be in the order of 1 cc to 5 cc, but this dosage will of course depend upon the physiology of the individual, including the size and depth of the target treatment site 50, the skin type of the individual, and the body size of the individual. The dosage can be determined by clinical study by physical measurements and titration, or can be selected empirically based upon general anatomic considerations, or a combination of these and other considerations.

As FIG. 7 shows, the method injects the light reactive agent 14 intravenously at the injection site 52. In the illustrated embodiment, the syringe 18 needle injects directly into a vein. An IV catheter may be used, through which the light reactive agent 14 is injected by syringe or other suitable IV pumping device.

The rate of delivery is dependent upon the nature and dosage of the light reactive agent 14 as well as the physiology of the individual being treated. It is desirable to avoid discomfort to the individual, and the rate of delivery selected has this as its primary objective.

It is believed that, given the concentration and volume of the VISUDYNE® material being injected in the illustrated embodiment, an injection period of 20 to 30 seconds is acceptable.

Figure 9:
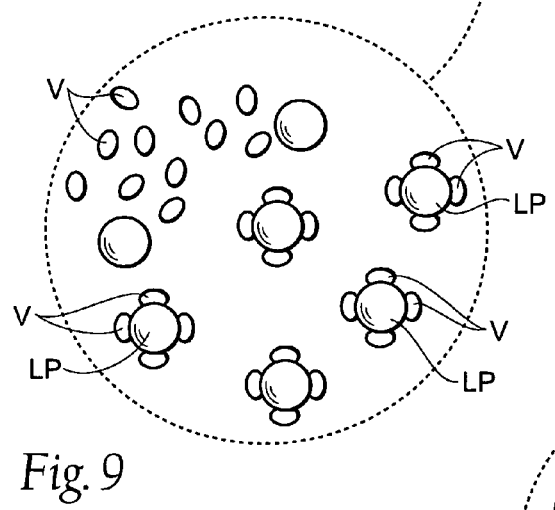
Figure 10:
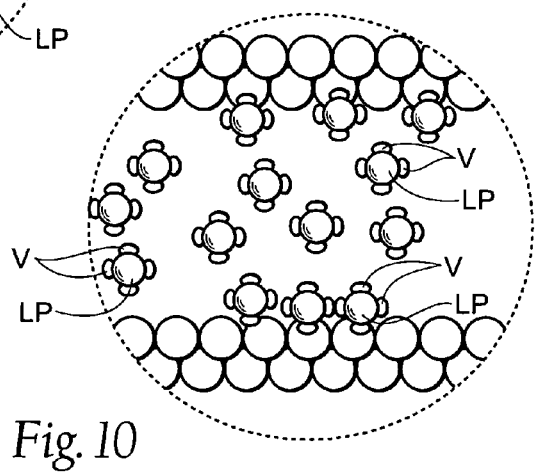

A period of time desirably occurs after injection (as the clocks C in FIGS. 7 and 8 indicate), to allow the light reactive agent 14 to become systemic. As FIG. 9 shows, verteporfin V, once injected, attaches to lipoproteins LP in the plasma. The lipoproteins LP carry the verteporin V to the targeted treatment site 50, as FIG. 10 shows. This exposes endothelium of the spider veins to the verteporin V carried by the lipoproteins LP.

The optimal time period to allow systemic distribution of the light reactive agent 14 in this manner to the targeted treatment site 50 following injection can be determined by clinical study by physical measurements, or can be selected empirically based upon general anatomic considerations, or a combination of these and other considerations.

Figure 11:
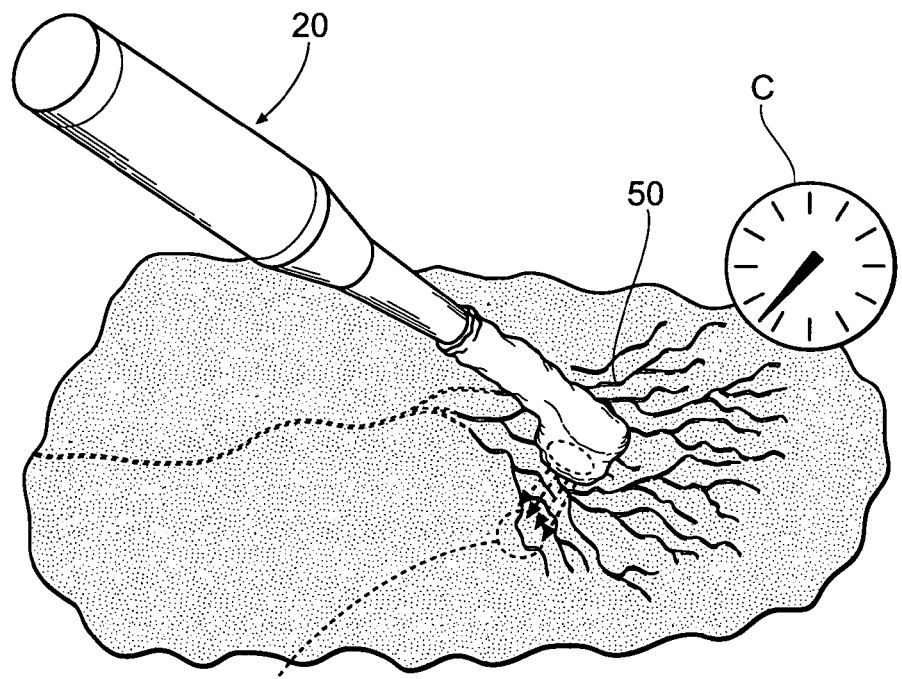

As FIG. 11 shows, after allowing a selected time period after injection to pass, the method operates the photoactivation device 20 to apply light having prescribed characteristics to the targeted treatment site 50. These prescribed characteristics include the wavelength and may also include, but are not necessarily limited to, a desired intensity, a desired spot size, and a desired duration of exposure. The wavelength will depend upon the light reactive agent 14 selected. The intensity, spot size, and duration of exposure of the applied light will depend upon the physiology of the individual being treated and the operating parameters of the system 10, e.g., upon the size of the treatment site 50; the depth of the treatment site 50; the skin type of the individual; the body size of the individual; the distance between the light transmitting end 28 of the housing 24 and the skin surface; the time of exposure; and the pattern of applying the light. Optimal operating characteristics for the photoactivation device 20 can be determined by clinical study by physical measurements, or can be selected empirically based upon general anatomic considerations, or a combination of these and other considerations. The photoactivation device 20 can apply light either without making direct contact with the skin or by making direct contact with the skin.

Figure 12:
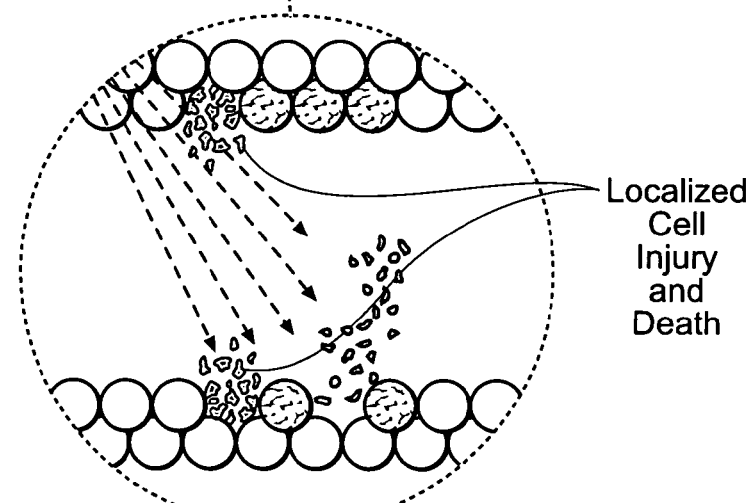

As FIG. 12 shows, once verteporfin is activated by light in the presence of oxygen, highly reactive, short-lived singlet oxygen and reactive oxygen radicals are generated. The singlet oxygen and reactive oxygen radicals cause local damage to inner wall or endothelium of the veins. Cells outside of contact with the activated verteporfin, however, are left unaffected.

Treatment by the system 10 and method just described intentionally causes injury to the inner vein walls. By controlling the clinically parameters above described (i.e., the dosage, delivery time and rate, operating conditions of the photoactivation device 20, etc.,) the nature of the injury can be tightly controlled and localized.

Figure 13:
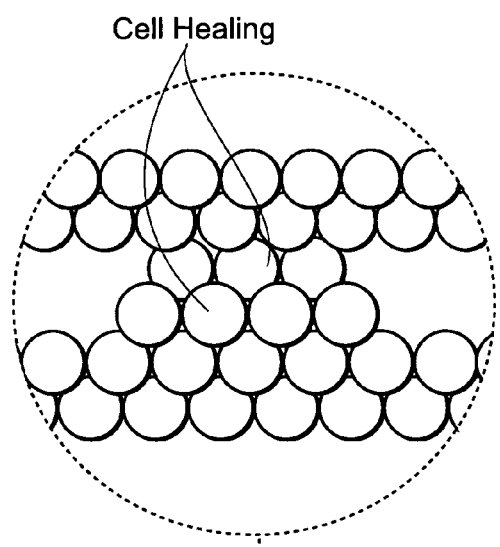
Figure 14:
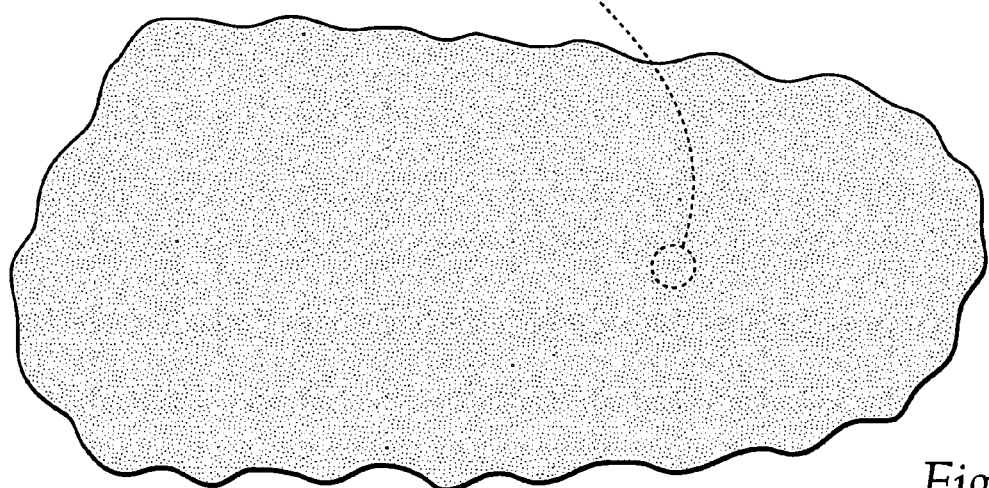

The initial injury to the vein wall evokes a healing process (see FIG. 13). During the healing process, the vein heals shut over time. The healing results in shrinkage of the spider vein, and eventually, complete obliteration of the spider veins in the targeted region, as FIG. 14 shows.

It should be appreciated that the devices, systems, methods, and protocols that have been described can provide minimally invasive, cost effective, and patient-friendly treatment of diseases or dysfunctions in all regions of the body that can be readily accessed by treatment agents carried by blood; e.g., cancers like breast and prostrate cancer; ear, nose, and throat conditions; periodontal disease; and diseases of the eye.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method for treating a spider vein comprising
identifying a targeted treatment site where a spider vein exists,
identifying an intravenous injection site offering venous access to the targeted treatment site spaced at a distance from the targeted treatment site,
providing a prescribed volume of a photosensitizing agent in solution that, when exposed to a source of light energy at a selected wavelength, generates singlet oxygen and free radicals without generating heat,
injecting the prescribed volume of the photosensitizing agent in solution at the intravenous injection site,
waiting a prescribed time period to allow the photosensitizing agent in solution to become systemic and be carried by blood into contact with endothelial tissue of an inner wall of the spider vein,
applying light energy percutaneously to the targeted treatment site, the light energy having the selected wavelength that activates the photosensitizing agent to generate singlet oxygen and reactive oxygen radicals that disrupt normal cell functions and cause intentional endothelial tissue cell death in the inner wall of the spider vein and evoke a healing process without affecting tissue cells outside the spider vein, and
allowing the healing process to shut and shrink the spider vein in the targeted treatment site.

2. A method according to claim 1
wherein the photosensitizing agent comprises verteporfin.

3. A method according to claim 1
wherein the light energy comprises light from at least one light emitting diode.

4. A method according to claim 1
wherein the light energy is applied by a hand-held photoactivation device.

5. A method according to claim 4
wherein the photoactivation device is battery powered.

* * * * *